United States Patent

Collura

[11] Patent Number: 5,899,867
[45] Date of Patent: May 4, 1999

[54] SYSTEM FOR SELF-ADMINISTRATION OF ELECTROENCEPHALOGRAPHIC (EEG) NEUROFEEDBACK TRAINING

[76] Inventor: Thomas F. Collura, 8122 Westhill Dr., Chagrin Falls, Ohio 44023

[21] Appl. No.: 08/728,763

[22] Filed: Oct. 11, 1996

[51] Int. Cl.[6] .................................................. A61B 5/0482
[52] U.S. Cl. ............................................ 600/545; 600/27
[58] Field of Search ............................... 600/27, 28, 544, 600/545, 596

[56] References Cited

U.S. PATENT DOCUMENTS

| | | |
|---|---|---|
| 4,320,768 | 3/1982 | Ledley et al. . |
| 4,474,186 | 10/1984 | Ledley et al. . |
| 4,747,082 | 5/1988 | Junker ...................................... 600/545 |
| 4,919,143 | 4/1990 | Ayers . |
| 4,928,704 | 5/1990 | Hardt . |
| 4,949,726 | 8/1990 | Hartzell et al. . |
| 4,955,388 | 9/1990 | Silberstein . |
| 5,010,891 | 4/1991 | Chamoun . |
| 5,024,235 | 6/1991 | Ayers . |
| 5,123,899 | 6/1992 | Gall . |
| 5,135,468 | 8/1992 | Meissner . |
| 5,213,562 | 5/1993 | Monroe . |
| 5,220,921 | 6/1993 | Ferris et al. . |
| 5,224,864 | 7/1993 | Vavaglakis . |
| 5,241,967 | 9/1993 | Yasushi et al. . |
| 5,267,942 | 12/1993 | Saperston . |
| 5,289,438 | 2/1994 | Gall . |
| 5,295,491 | 3/1994 | Gevins . |
| 5,306,228 | 4/1994 | Rubins . |
| 5,320,109 | 6/1994 | Chamoun et al. . |
| 5,325,872 | 7/1994 | Westermann . |
| 5,331,969 | 7/1994 | Silberstein . |
| 5,352,181 | 10/1994 | Davis . |
| 5,356,368 | 10/1994 | Monroe . |
| 5,363,858 | 11/1994 | Farwell . |
| 5,365,939 | 11/1994 | Ochs . |
| 5,374,193 | 12/1994 | Trachtman . |
| 5,377,258 | 12/1994 | Bro . |
| 5,406,957 | 4/1995 | Tansey . |
| 5,447,166 | 9/1995 | Gevins . |
| 5,450,855 | 9/1995 | Rosenfeld . |
| 5,458,117 | 10/1995 | Chamoun et al. . |
| 5,465,729 | 11/1995 | Bittman et al. .......................... 600/545 |
| 5,467,777 | 11/1995 | Farwell . |

Primary Examiner—Danton D. DeMille
Assistant Examiner—David M. Ruddy
Attorney, Agent, or Firm—Calfee, Halter & Griswold LLP

[57] ABSTRACT

A system for self-administered monitoring, displaying, analyzing and recording electrical activity of the brain provides indications of brain activity and a corresponding mental state of a user. A plurality of visual, auditory and tactile feedback mechanisms are integrated with the presentation of control and notification indications, to facilitate neurofeedback training of the user, The operational interface and sequencing is provided in such a manner as to provide the ability to the user to record, manage and control brain activity for different purposes including self-improvement, treatment, peak performance and recreation.

8 Claims, 14 Drawing Sheets

SYSTEM FOR SELF-ADMINISTRATION OF ELECTROENCEPHALOGRAPHIC (EEG) NEUROFEEDBACK TRAINING

FIELD OF THE INVENTION

The present invention pertains generally to EEG biofeedback for learning and controlling bio-electric characteristics of the brain which correspond to different mind states and conditions and, more particularly, to self-administered biofeedback systems which allow the user to provide interactive input in response to biofeedback neurologic signals to maintain or vary a mental state.

BACKGROUND OF THE INVENTION

EEG (brainwave) signals have been extensively studied in an effort to determine relationships between frequencies of electrical activity or neural discharge patterns of the brain and corresponding mental, emotional or cognitive states. Biofeedback of identified frequency bands of EEG signals is used to enable a person to voluntarily reach or maintain a target mental state.

Frequency bands of EEG readings used in such biofeedback have been generally categorized in the approximate frequency ranges of:

delta waves, 0 to 4 Hz;
theta waves, 4 to 7 Hz;
alpha waves, 8 to 12 Hz;
beta waves, 12 Hz to 36 Hz, and
sensorimotor rhythm (SMR) waves, 12 to 15 Hz.

It is theorized that each of the major subbands of biofeedback EEG (delta, theta, alpha, beta) has unique bio-electric characteristics which correspond with unique subjective characteristics of an individual. The delta band is observed most clearly in coma and deep sleep, the theta band in light sleep and drowsiness, the alpha band in a variety of wakeful states involving creativity, calm and inner awareness, and the beta band in alert wakeful situations with external focus. In general, a dominant brain wave frequency increases with increasing mental activity.

Many different approaches have been taken to EEG biofeedback to achieve mental state control. U.S. Pat. No. 4,928,704 describes a biofeedback method and system for training a person to develop useful degrees of voluntary control of EEG activity. EEG sensors are attached to cortical sites on the head for sensing EEG signals in a controlled environmental chamber. The signals are amplified and filtered in accordance with strict criteria for processing within time constraints matching natural neurologic activity. The signals are filtered in the pre-defined subbands of alpha, theta, beta and delta, and fed back to the monitored person in the form of optical, aural or tactile stimuli.

U.S. Pat. No. 4,949,726 discloses an electrical device which is responsive to recorded brain waves to produce an electrical output which corresponds to detection of brain waves in predefined frequency ranges. The output of the device is connected to a device control apparatus to cause an output device to perform a function in accordance with detected brainwave signals. U.S. Pat. No. 5,024,235 describes an EEG neurofeedback apparatus which detects analog signals from the brain, converts readings to digital signals and compares the digital signals to a threshold amplitude to provide an auditory or visual indication to a person of whether or not the detected signals are within a predetermined frequency range.

U.S. Pat. No. 5,241,967 describes a system for evoking EEG signals from a subject which applies a frequency signal to a stimulus generator for conversion to a stimulative signal such as a photic stimulus to the subject. The brain wave to be evoked is strongly synchronized by the stimulative signal applied to the subject to put the subject in the desired brain wave state. U.S. Pat. No. 5,365,939 describes a method for evaluating and treating an individual with EEG disentrainment feedback by selecting a reference site to determine a reference brain wave frequency, entraining the brain wave frequency in one direction until a first stop condition occurs, the entraining the brain wave frequency in an opposite direction until a second stop condition occurs. Different electrode sites are selected to fully test an individual for flexibility to EEG entrainment feedback treatment. And U.S. Pat. No. 5,406,957 describes an EEG Neurofeedback apparatus for training and tracking of cognitive states which measures bioelectric signals in bandwidth windows to produce a composite amplitude by a fast Fourier transform on an amplified signal. Selected bandwidths are displayed and monitored by computer to enable training of a person being monitored with audio or verbal feedback.

In many of the EEG biofeedback systems and methods of the prior art, it is necessary to interrupt data collection and analysis and/or the biofeedback process in order to perform set-up functions, to review component values, or to set protocols or adjust threshold levels. These functions are typically performed by a session administrator, which can ultimately diminish or otherwise adversely effect the nature and quality of biofeedback signals to a subject seeking to benefit from EEG training.

Most of the neurofeedback systems of the prior art generate only a single form of each type of feedback stimuli, such as a single screen display, or a single auditory and tactile signal, thus inherently limiting the scope of biofeedback and physical (EEG) response.

SUMMARY OF THE PRESENT INVENTION

The present invention provides a method an apparatus for self-administration of electroencephalographic (EEG) neurofeedback training which records and analyzes electrical activity of the brain and produces an indication of a corresponding mental condition or state to a user.

In accordance with one aspect of the invention, a system for self-administration of EEG neurofeedback training includes an EEG monitor having an EEG amplifier, an isolated computer interface, a microprocessor controller, and a peripheral breadboard area, EEG electrodes connected to the EEG module for attachment to the head of a user of the system, a connection from the EEG module isolated interface to a computer, the computer programmed with software of the system for monitoring, recording, reading, analyzing and displaying EEG signals, a monitor connected to the computer for display images of EEG signals processed by the computer and the system software.

In accordance with another aspect of the invention, a method for self-administration of electronencephalographic (EEG) neurofeedback training through observation and control of displayed graphic images which correspond in real time to EEG signals obtained from a user of the system includes the steps of connecting electrodes of an EEG neurofeedback training system to the head of a user, the system having an EEG module connected to the electrodes and to a computer, the computer having software for receiving and analyzing signals received from the electrodes and generating screen displays in response to received EEG signals, the software further having control functions including user selection of types of screen displays including combinations of types of screen displays generatable by the software in response to EEG signals, and user selection of screen display parameters which correspond to received EEG signals, selecting a screen display for generation by the software and display on a monitor connected to the computer, selecting screen display parameters, and viewing the screen display generated by the software in response to received EEG signals.

These and other aspects of the invention are herein described in particularized detail with reference to the accompanying Figures.

DETAILED DESCRIPTION OF PREFERRED AND ALTERNATE EMBODIMENTS

Figure 1:
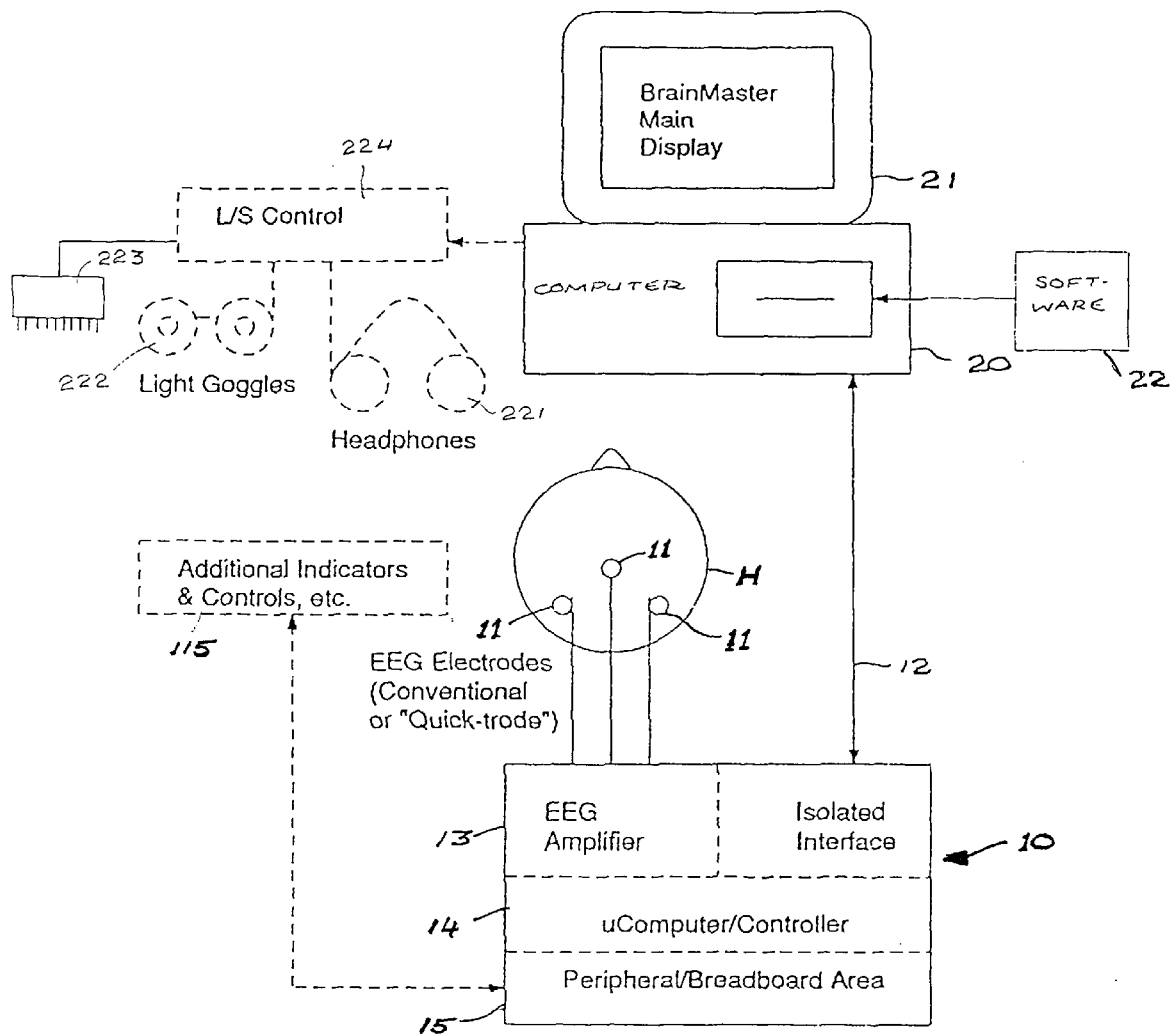
FIG. 1 is a schematic representation of the hardware components of the system of the present invention.

With reference to FIG. 1, there is illustrated the basic components of the apparatus of the invention including an EEG module 10 having at least three EEG electrodes 11 connected thereto and attachable to the head H of a user. The EEG module 10 is connected by a serial data line 12 to a computer or data processor 20 which is connected to a display monitor 21, and/or addition biofeedback stimulative devices such as audio or vibratory headphones 221, light goggles 222, and/or tactile stimulator 223 as controlled by a feedback device controller 224 connected to computer 20. Computer 20 contains EEG analysis and biofeedback software 22 which performs EEG recording, analysis and biofeedback operations as described herein.

The EEG module 10 includes a 2-channel EEG amplifier 13; a computer/controller 14, and on a peripheral breadboard area 15 a built-in electrode test and connection to additional indicators and controls indicated generally at 115; 2 auxiliary channels (GSR, Temp); analog-to-digital converter (1–8 channels); 8-bit digital input port; 8-bit digital output port; optically isolated RS-232 port (9600 baud), and rechargeable batteries. The system uses an internal control structure that exploits the presence of two, independently operating computer units in the form of EEG module 10 and computer 20. The EEG module 10 is clocked by an internal interrupt timer that is responsible for initiating a processing cycle. The computer 20 is, for example, an Intel-based PC with a 486/50 or Pentium processor with Windows to include local storage and graphics, and also uses an internal interrupt timer responsible for initiating the processing cycle. The two computers, when operating concurrently, undertake a cyclic method of operation which facilitates two main computing functions: (1) the acquisition and transmission of data by the module, and the receipt of data, processing, and display by the user computer, and (2) the determination and transmission of control information by the user computer, and the receipt of this information by the module, which then carries out any of a number of possible user-feedback tasks.

Figure 2:
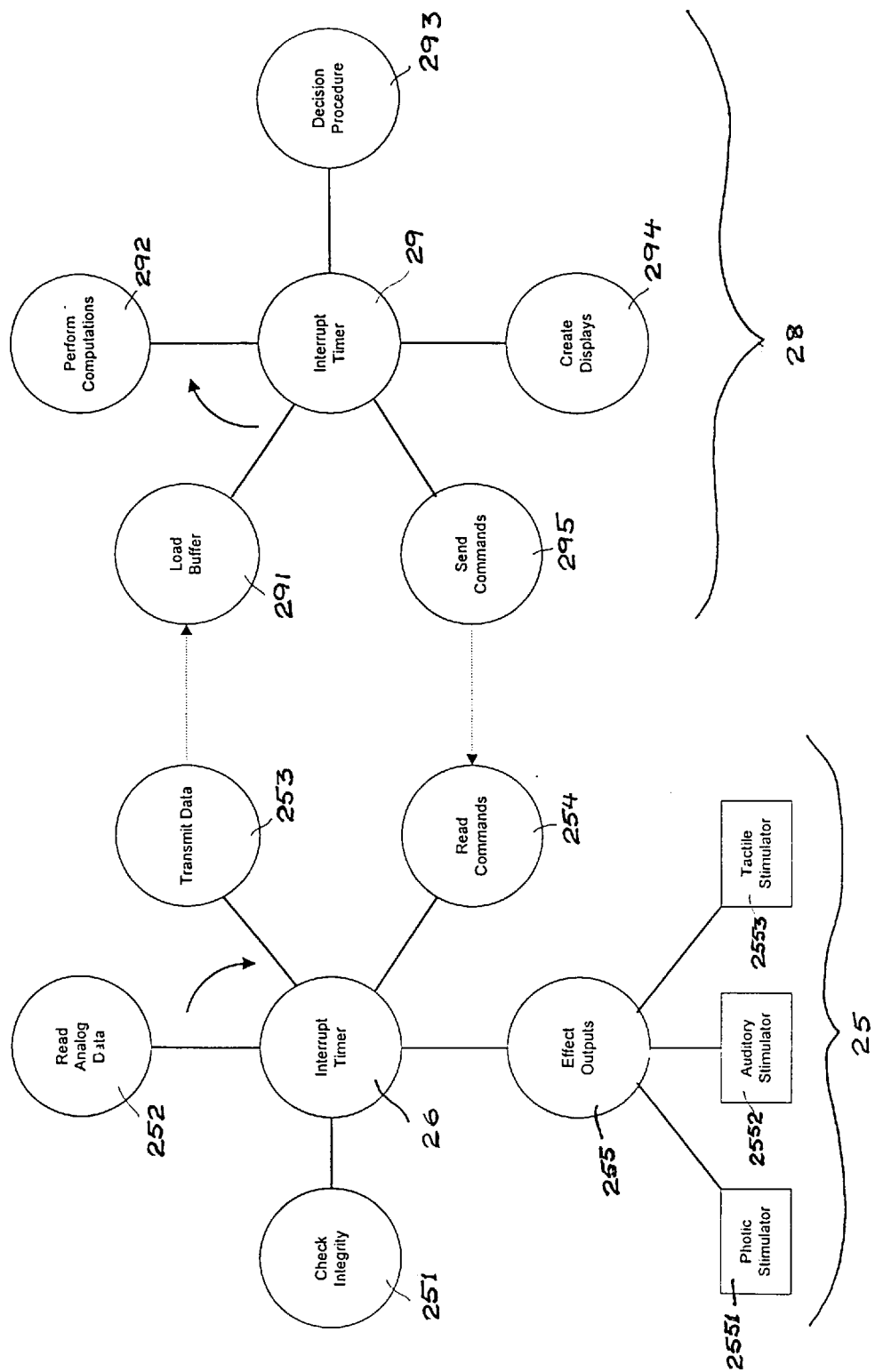
FIG. 2 is a schematic diagram of the hardware and software control scheme of the invention.

The supervisory functions of the system are identified as: Sequence Timing and Control, User Information and Instruction, and Spoken Report and Command. With reference to FIG. 2, the system uses an internal control structure that exploits the presence of two, independently operating, computer units. The first, computer 25 is clocked by an internal interrupt timer 26 that is responsible for initiating a processing cycle including an integrity check 251, analog data read 252, data transmission 253, data read 254, and output effects 255, including for example photic stimulator 2551, auditory stimulator 2552, and/or tactile stimulator 2553. The second computer 28, which is for example a computer workstation including local storage and graphics, also uses an internal interrupt timer 29, that is responsible for initiating the processing cycle in accordance with the software of the invention, which includes for example the steps of loading the buffer at 291, performing computations at 292, decision procedure 293, creation of displays at 294, and sending of commands at 295. These two computers, when operating concurrently, undertake a cyclic method of operation that facilitates two main processes: (1) The acquisition and transmission of data by the module, and the receipt of data, processing, and display by the user computer, and (2) the determination and transmission of control information by the user computer, and the receipt of this information by the module, which then carries out any of a number of possible userfeedback tasks.

The EEG module is powered by a rechargeable battery power circuit. When the unit is turned off, the power from the 9VDC adapter plugged into the 120 VAC line is used to charge the internal battery. The circuit interrupts current from reaching the user, even with electrodes connected to the user. When the unit is turned on, the line is disconnected and the module operates from the batteries. This also insulates the user from the electrical energy which powers the module. The circuit thus uses AC line power to sustain the battery, which also remains connected to the wall-mounted power supply at all times, but without the risk associated with using line power to the module, thus eliminating any possibility of electrical shock to the user.

Software 22 provides computing functions for data acquisition; graphic display (multiple modes); FFT frequency transform; EEG frequency band measurement; biofeedback task control and recording; file save and restore, graphing and summary capabilities. With the EEG module 10 and computer 20 connected and powered up, the software 22 is booted to generate an initial "open-input" noise display as shown in FIG. 3, representing the high frequency noise that is typically picked up by the EEG module 10 when it is sitting with nothing connected to the EEG module inputs.

The electrodes 11 of the EEG module are attached to the user as, for example to the locations illustrated in FIG. 1, one electrode to each ear, and to at least one location on the scalp, with preferably one on each side of the forehead to provide "right active" and "left active" two-channel input, and neutral (or "indifferent") and "ground" EEG inputs. Generally, the active electrode will be attached to the head in a specific location (frontal, parietal, occipital, etc.), and the indifferent and ground electrodes will be attached to each ear. The active and indifferent electrodes are fed to either channel of the EEG module 10. For example, with the active electrode attached to the head, the indifferent electrode attached to the left ear, and ground attached to the right ear, the EEG module will measure brainwave activity between the head and the left ear as a reference, with the right ear being used as ground. Two active leads (right and left) provide two channel EEG monitoring. A dual ear clip can be used to provide connections on both the front and back of the ear. Using this electrode, a single channel recording (e.g., the left channel as shown) is obtained with only a single head connection. To add a second channel, a conventional earclip is added (e.g., to the right ear) and a second head connection ("right active") is attached.

Figure 3:
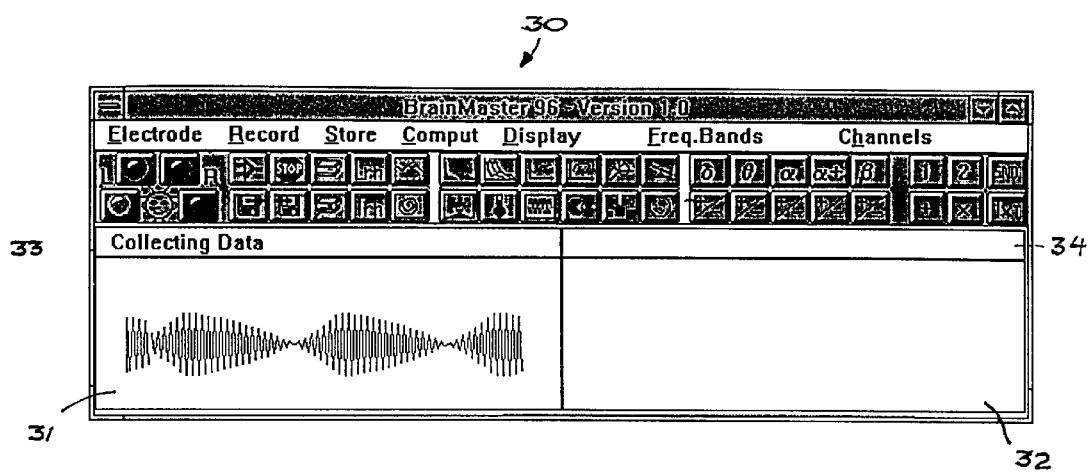
FIG. 3 is a screen display generated by the system of the present invention.

The program software 22 allows channel selection via the "1" and "2" buttons on the upper row of the toolbar shown in FIG. 3. The program starts up assuming a 1-channel module. If "2" is selected, the program assumes that the module is transmitting 2 channels of data. As represented by FIG. 3, one program screen display 30 generated by the software is divided vertically into two sides or window 31 and 32, denoted on the toolbar as "left" and "right". These two sides usually reflect the EEG activity from the respective sides of the brain. The work area consists of "tiled" regions that provide the various types of displays. The program generates the following alternative display windows: a report window in the upper left text window 33 presents text which explains what the system is doing, such as "programming module", or "collecting data". A "command window" in the upper right text window 34 presents text which requests user action such as "check module" or "relax for recording".

The system is capable of displaying any combination of a set of selectable windows, which can be reconfigured and displayed, or hidden, at any time, including when the system is in operation. Moreover, the windows operate in concert, providing a user-interface that exploits the presentation of information in various forms, and with the information in a window-relating to, or controlling, the information in another window. This provides the user with the ability to configure display and control screens that implement particular "protocols" for various purposes.

Figure 4:
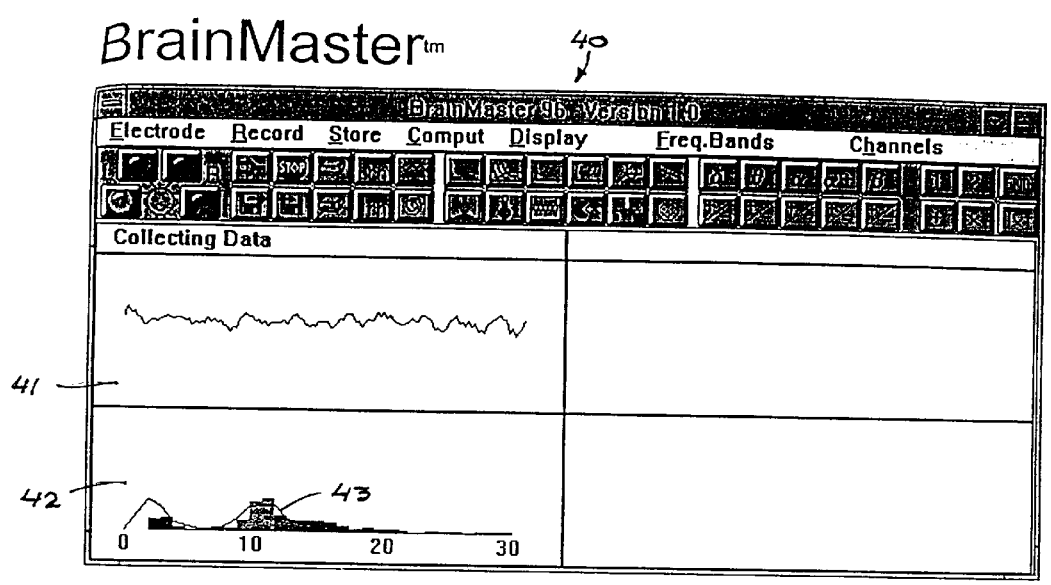
FIG. 4 is a combined EEG signal screen display generated by the system of the invention.

FIG. 4 illustrates an EEG wave form display 40 which, in window 41, displays a scrolling raw wave form (in for example a one second epoch) set to refresh approximately twenty times per second. The wave form is drawn left to right across the display window and when it reaches the end, the drawing position starts over at the left side, replacing the previous data as it moves across the window, thereby displaying one second of EEG at all time, thereby continuously displaying one second of EEG monitoring, without disturbing the neurofeedback training session. This capability is essential in the application of self-administered biofeedback training because it eliminates the need for a dedicated operator or session administrator to monitor waveforms, independent of the subject's activity.

Window 42 contains a Fast Fourier transform (FFT) display of a signal frequency spectrum of 1 to 30 Hz. This spectrum is updated four times per second and reflects the last one second of EEG data. A slowly changing "trend" envelope 43 is also superimposed to show the shape of the spectrum reflecting the last few seconds of EEG activity. This trend line is actually a "weighted" average of the past activity, using a wave length factor of approximately 0.6, so that the value of a point is, for example, 0.4×(current value)+0.6×(previous value), to provide a "smoothing" function. FIG. 4 also illustrates the simultaneous and combined display of alternative graphical representations of monitored EEG waveforms, which is a fundamental concept of the invention.

Figure 5:
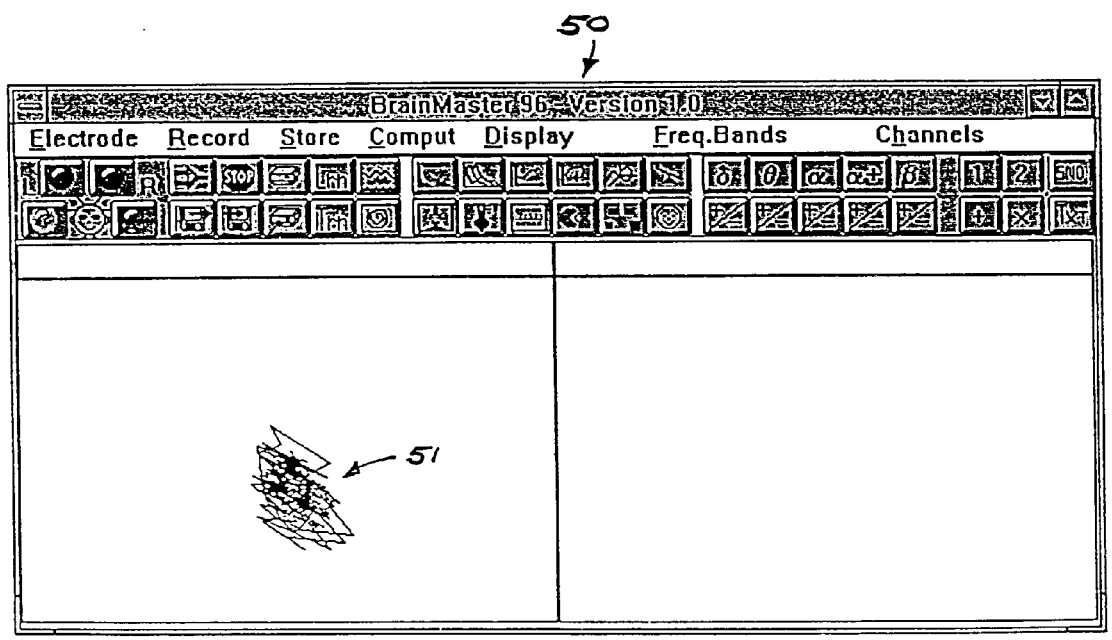
FIG. 5 is a two-dimensional plot EEG signal screen display generated by the system of the invention.

As shown in FIG. 5, the program further produces a "phase-space" two-dimensional display 50 using "rate of change" in place of the time axis, as commonly used in chaos analysis. The vertical axis is exactly the same as in the EEG wave form display, e.g., "amplitude" while the horizontal axis is the "first derivative" or "rate of change" of the EEG signal. This display produces very smooth coherent wave forms which appear as founded, open circles, while faster irregular activity will produce flatter shapes with more internal detail such as plot 51.

Figure 6:
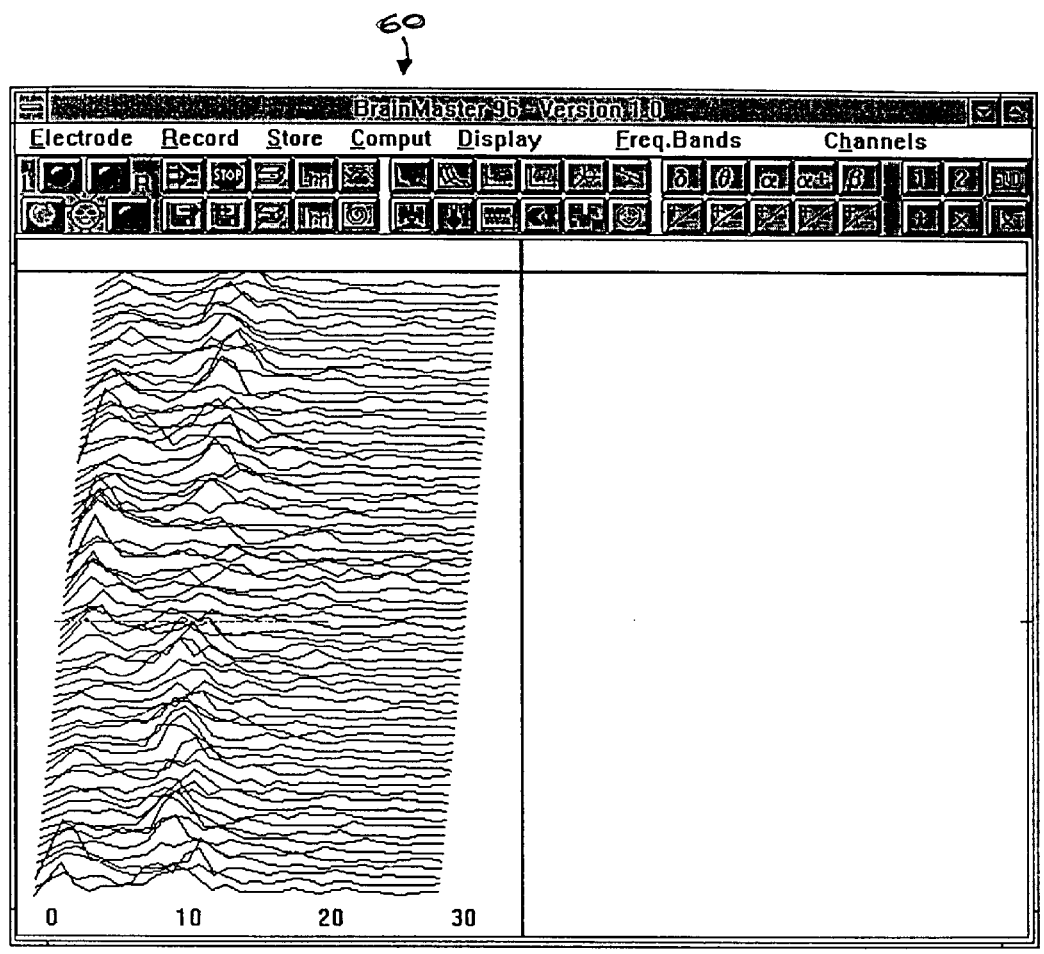
FIG. 6 is a compressed spectral array EEG signal screen display generated by the system of the invention.
Figure 7:
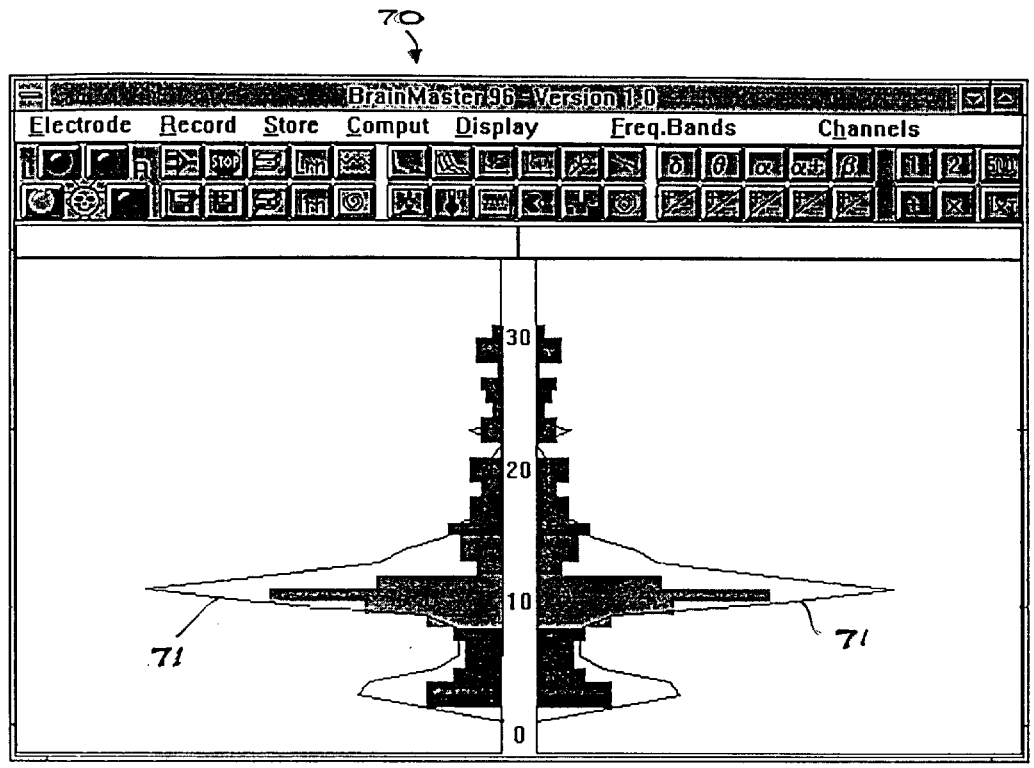
FIG. 7 is a laterally opposed bifurcated screen display generated by the system of the invention.

As shown in FIG. 6, the program alternatively can produce a compressed spectral array (CSA) display 60 which generates a cascade of past FFT spectra covering the previous 100 seconds of EEG activity. As shown in FIG. 7, the program alternatively can produce a symmetrical laterally opposed bar graph plot display 70 which includes smoothing trend lines 71 similar to that described in connection with FIG. 4.

Figure 8:
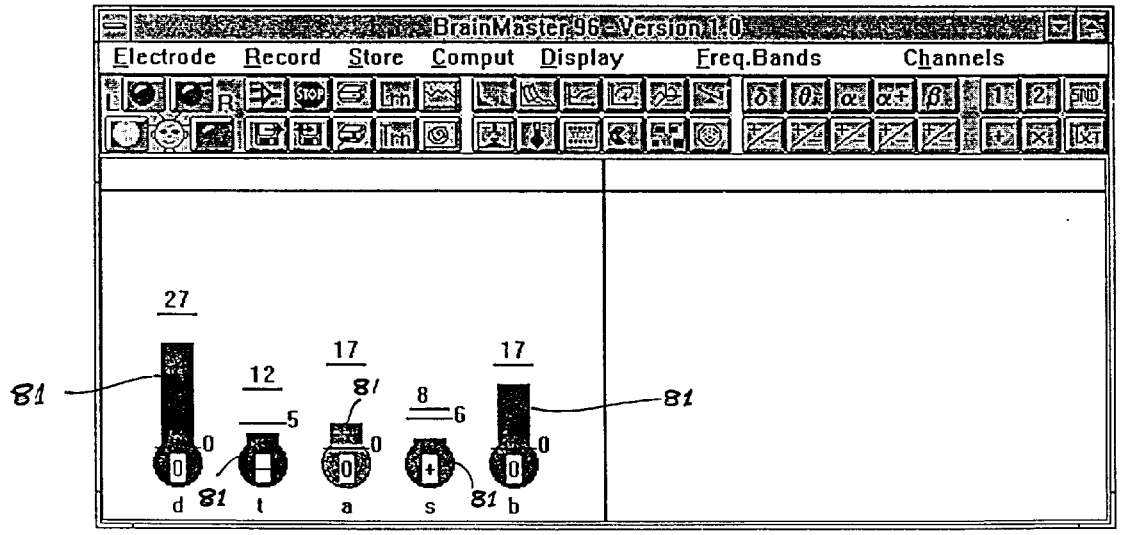
FIG. 8 is a thermometer EEG signal screen display generated by the system of the invention.

The program of the invention can alternatively produce a thermometer type display 80 as shown in FIG. 8, which includes each of the major EEG components or frequency band intensities as vertically oriented colored thermometers or "thermobars" 81 which vertically grow and shrink in real-time response to monitored EEG signals. In the thermometer type display of the invention, the EEG components or frequency bands represented by the individual thermometer columns are: Δdelta: (1–3 Hz), theta: (3–8 Hz), α alpha (8–12 Hz); SMR: (12–15 Hz), β beta: (15–32 Hz). The parameters of the frequency bands represented by the thermometer columns can be adjusted or reset by the user. The "temperature" of each thermometer or thermobar 81 reflects the summed energy in the frequency bands. Thus, they represent a combination of all the frequencies and are not a simple real time amplitude. However, they are proportional to the amplitude of all of the components combined, because they are scaled in the same units as the FFT and mind-mirror windows, both of which reflect signal energy in the "root mean square" sense.

In addition to displaying the EEG energy in each band, the thermometer display 80 of the invention is used to set up the biofeedback paradigms of the invention, which includes the identified components to be rewarded or to be discouraged, in the threshold values at which to elicit biofeedback signals. Each thermometer has superimposed on it two tick marks. The thicker top bar indicates the maximum value that a component has reached in a given current session. The thinner lower bar indicates the current threshold for the detection of activity in that band. With the "SND" mode enabled, every time the signal exceeds the threshold, there is generated an audible indication in the form of a spoken voice saying the name of the component, for example, "alpha", "beta".

Initially, the thresholds are auto-set during "learn" mode at either 60% of the maximum value ("4+ components" and 40% of the maximum value for ("−4 components") that have been reach in that session. Manual adjustment can then be easily done using the keyboard as described below. By displaying any combination of components, the thermometer display facilitates complex biofeedback paradigms with a single, simple, on-screen metaphor without interruption of EEG data collection and/or biofeedback to perform the setup function.

Figure 9:
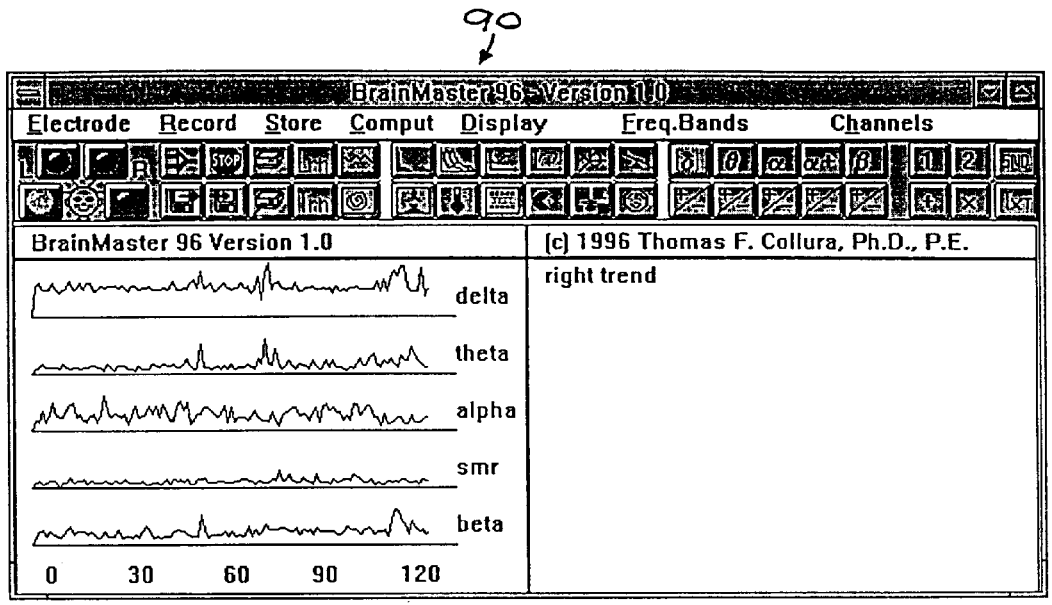
FIG. 9 is a scrolling wave form EEG signal screen display generated by the system of the invention.

The software can alternatively generate one dimensional trends of each of the biofeedback EEG frequency bands to show current and past activity of a component in a plot of value vs. time over a period of 120 seconds, as shown by the display 90 in FIG. 9. After the plot reaches 120 seconds, it clears and redraws. The plot window displays only those components which are currently selected, i.e. that would be displayed in the "thermometer" window. Trend values are saved in a disk file so that any number of successive two minute periods can be saved to the file for later display and analysis. All components are calculated and saved to a trend file whether they are displayed or not.

Figure 10:
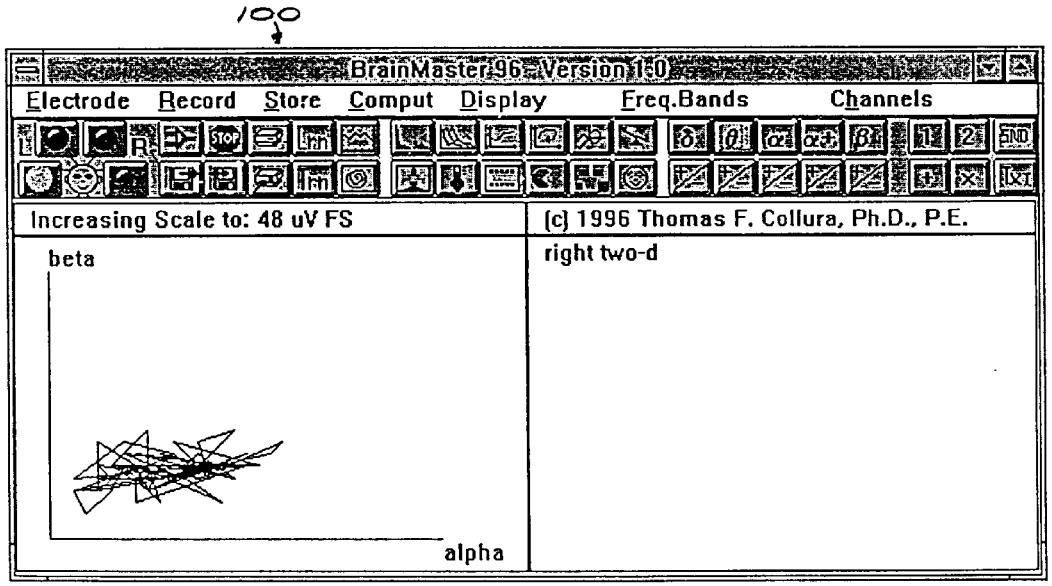
FIG. 10 is an alpha-beta EEG signal plat screen display generated by the system of the invention.

Alternatively, a two dimensional trend displays plots components against each other, such as, for example, alpha vs. beta as shown in the display 100 of FIG. 10. This plot uses the first two of the currently selected components in order from low frequency to high frequency, i.e., delta, theta, alpha, SMR, beta.

Figure 11:
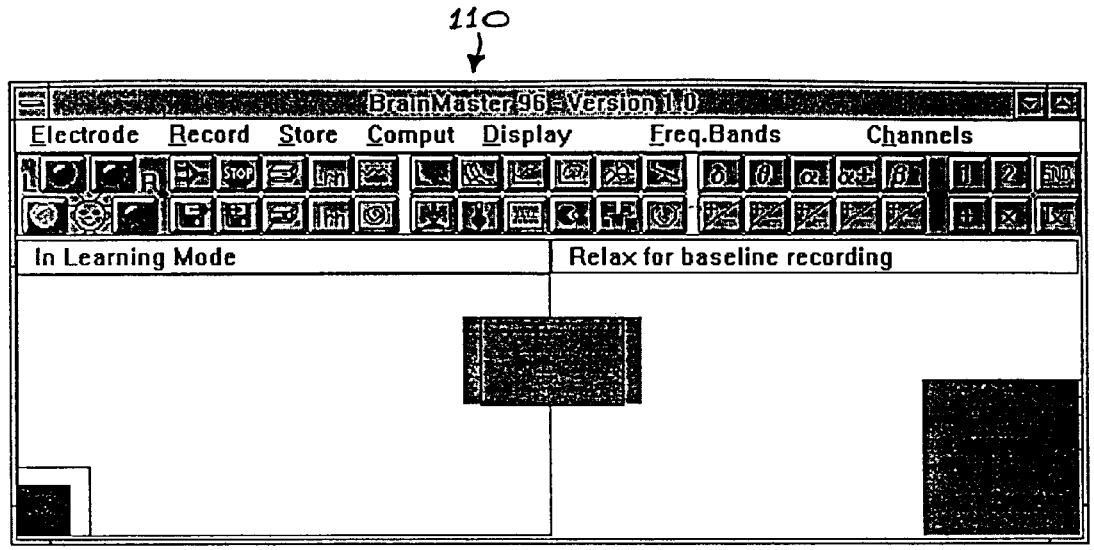
FIG. 11 is a two-dimensional block EEG signal screen display generated by the system of the invention.

The system software can alternatively generate a "highway" type display 110 shown in FIG. 11 which is similar to an EEG spectrum, used for ADD protocols with theta, SMR and beta as three colored bars, with the center bar proportional to SMR, the left bar proportional to theta, and the right bar proportional to beta. The software generates the rectangular lines 111 which surrounding the boxes to provide a visual indication of current threshold values.

Figure 12:
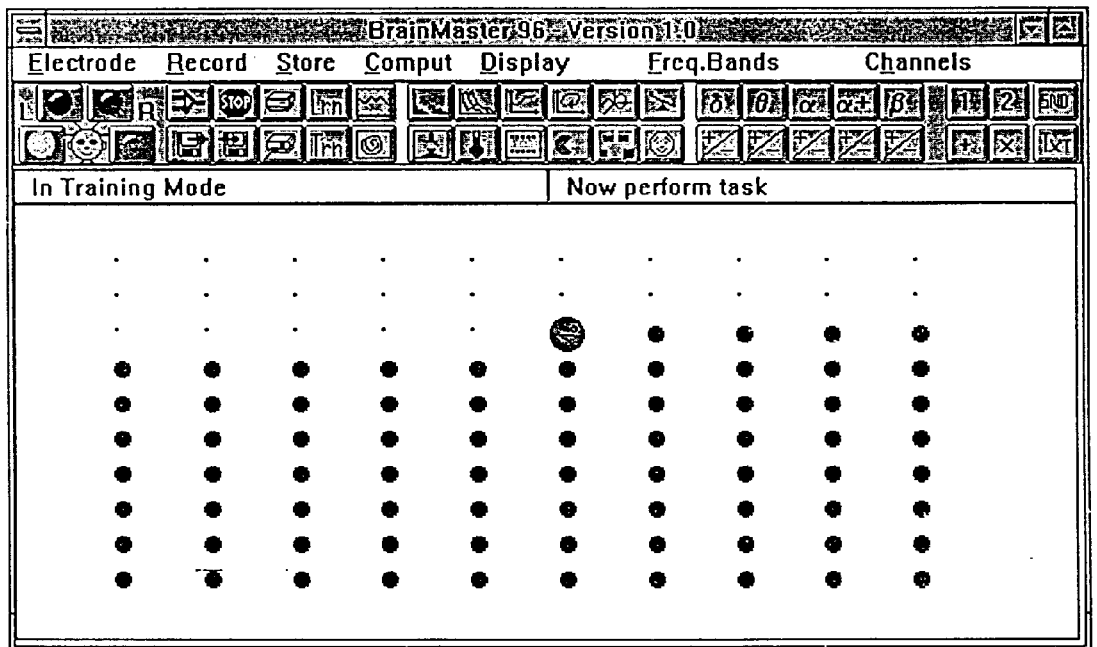
FIG. 12 is a sequentially dynamic columnar screen display generated by the system of the invention.

Alternatively, the system software can produce a "pac man" type display 120 shown in FIG. 12 which will advance one point for each target hit. Since what constitutes a "hit" is determined by the set up of the thermometer system, the exact criteria for causing the "pac man" to move can be set up in any desired fashion, such as an alpha or beta wave reinforcement.

Figure 13:
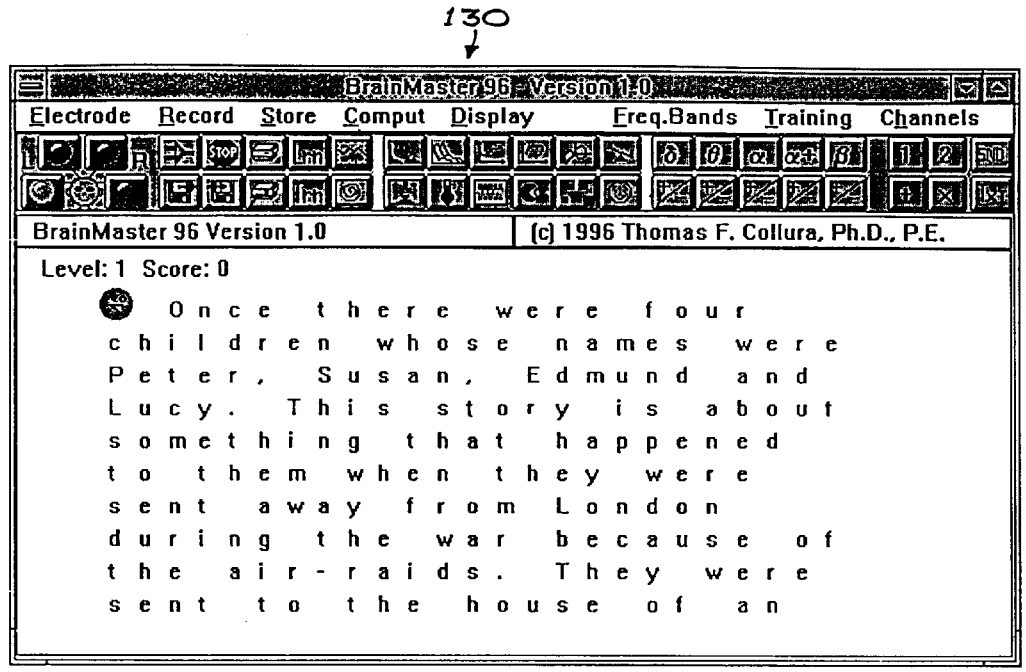
FIG. 13 is a sequentially dynamic row arranged screen display generated by the system of the invention.

Alternatively, the system software can produce a "pac man" with words or "word man" wherein the pac man will eat his words, as shown by display 130 in FIG. 13. This is very useful in working with people who wish to work with their EEG brain waves while reading. The word man display moves from level to level continuing to read from a file automatically "turning the pages" as the levels proceed. The user may type any text into a DOS text file and, by copying that file into a pac man file and restarting the pac man screen, the text is dynamically incorporated into the display.

Figure 14:
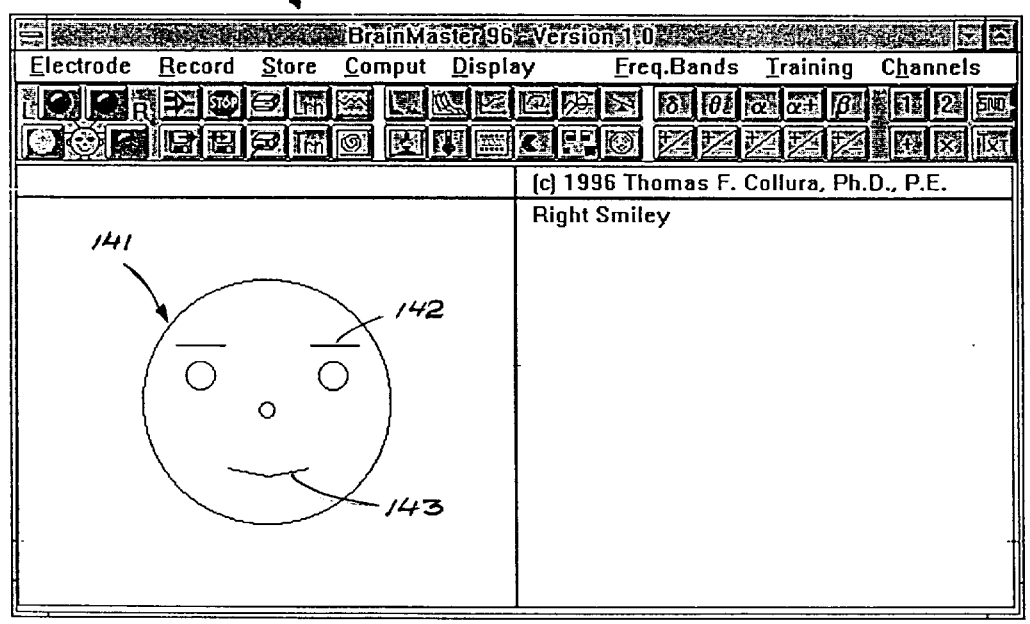
FIG. 14 is a facial expression screen display generated by the system of the invention.

As shown by display 140 of FIG. 14, the system of the invention can also produce an interactive biofeedback display which is generally in the form of an expressive facial image 141, the features of which are determined by the monitored EEG activity. This aspect of the invention allows the user to control the facial expression on the screen using the EEG waveforms. The angle of the eyebrows 142, and the angle of the smile (or frown) 143 are controlled by two EEG components. Thus, a range of expressions, including "happy," "mischievious," "hopeful," and "angry" can be produced by the different combinations of these facial features.

The face works in any mode, including training mode. Typically, the mouth is used to reflect a component we wish to encourage, and the eyebrows are used to reflect a component we wish to discourage. The degree of angle of the mouth, or of the eyebrows, is made relative to the threshold value. The center point of the mouth is set by the threshold value, and the outside of the mouth is set by the component controlling it. Thus, a mouth value below threshold is a frown, and a value above threshold is a smile. If the "threshold" values are not set, then they are taken to be zero. Thus, the mouth value would always be a smile, of varying extent.

In the case of the eyebrows, the controlling component sets the outer ("lateral") points, while the threshold sets the inner ("medial") points.

Thus, a value below threshold "lifts" the eyebrows, and a value above threshold "lowers" the eyebrows. "Lifting" the eyebrows means that the center of the eyebrows is higher than the outsides, resulting in a "positive" affect. "Lowering" the eyebrows can also be called "scowling," in which the center of the eyebrows is lower than the outsides. Similar to the mouth, if there is no threshold value, then the eyebrows are always relatively "lowered."

In the following examples, the mouth is controlled by the alpha (8–12) amplitude, and the eyebrows are controlled by the theta (4–7) amplitude. In accordance with some "ADD" protocols, we want to encourage alpha, and discourage theta. As alpha increases, the "smile" grows. On the other hand, as theta increases, the eyebrows "scowl." Other facial expression parameters can be incorporated into this display of the invention such as wide open or squinting eyes, moving nose, ears and other facial lines or contours which contribute to an overall expression such as dimples, wrinkles and cheek bone profiles. Also, digitized images of an actual user could be generated and digitally altered from memory to alter the described facial components according to monitored EEG signals.

Figure 15:
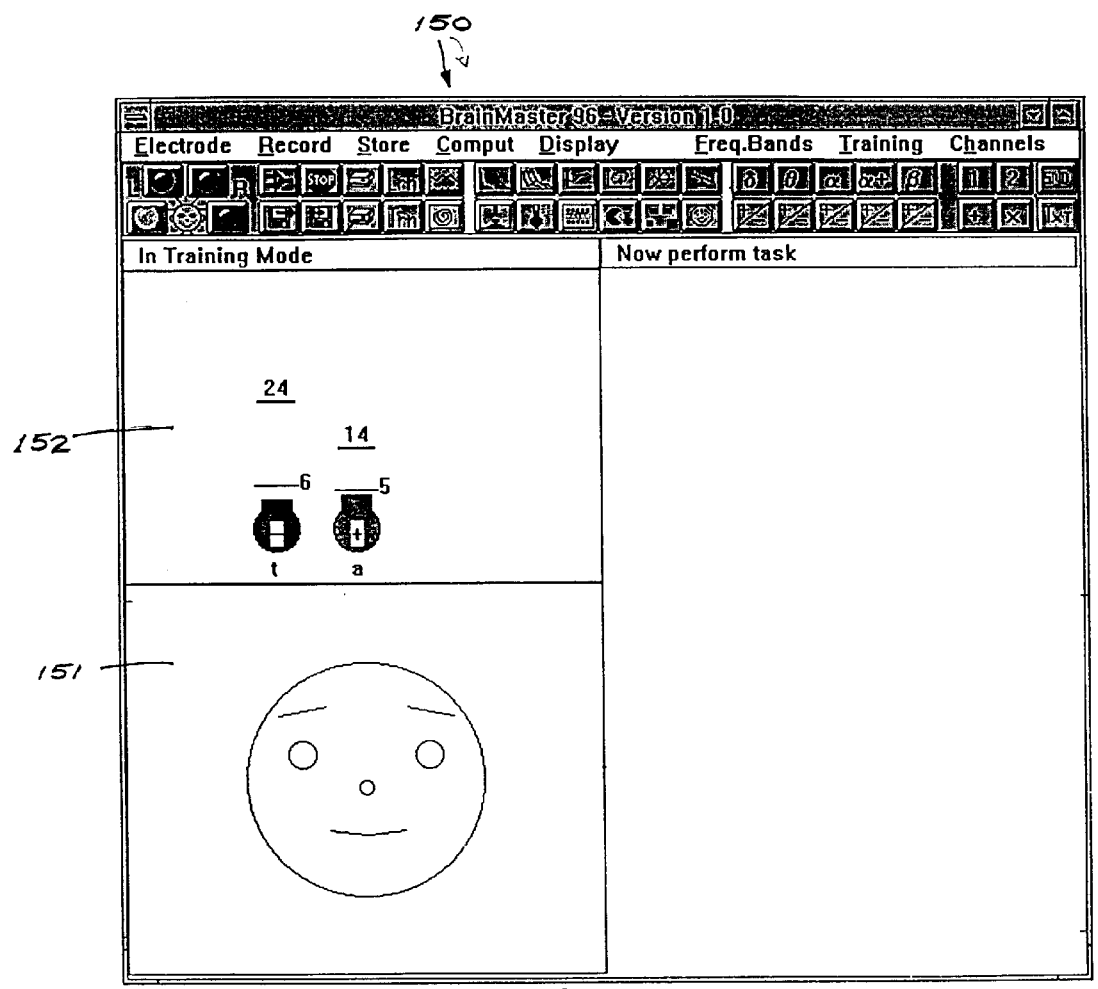
FIG. 15 is a combined screen display generated by the system of the invention.

As represented by the facial expression in display 150 of FIG. 15, both the alpha and the theta are relatively low. As a result, the face is not really smiling, but the eyebrows are lifted in response to the low theta. The face is hopeful, since the user is capable of keeping the theta low, but has not yet demonstrated enhanced alpha. As further shown by FIG. 15, the facial expression can be simultaneously displayed with any of the previously described biofeedback display formats such as the thermometer array 152, which readings of course correspond in real time to the elements of the facial expression. Such combined displays can be reconfigured or hidden at any time, including when the system is in operation. The display windows operate in concert to maximize the feedback effectiveness of the combined formats. This feature provides the user with the ability to configure display and control screens which implement particular protocols for various purposes.

Figure 16:
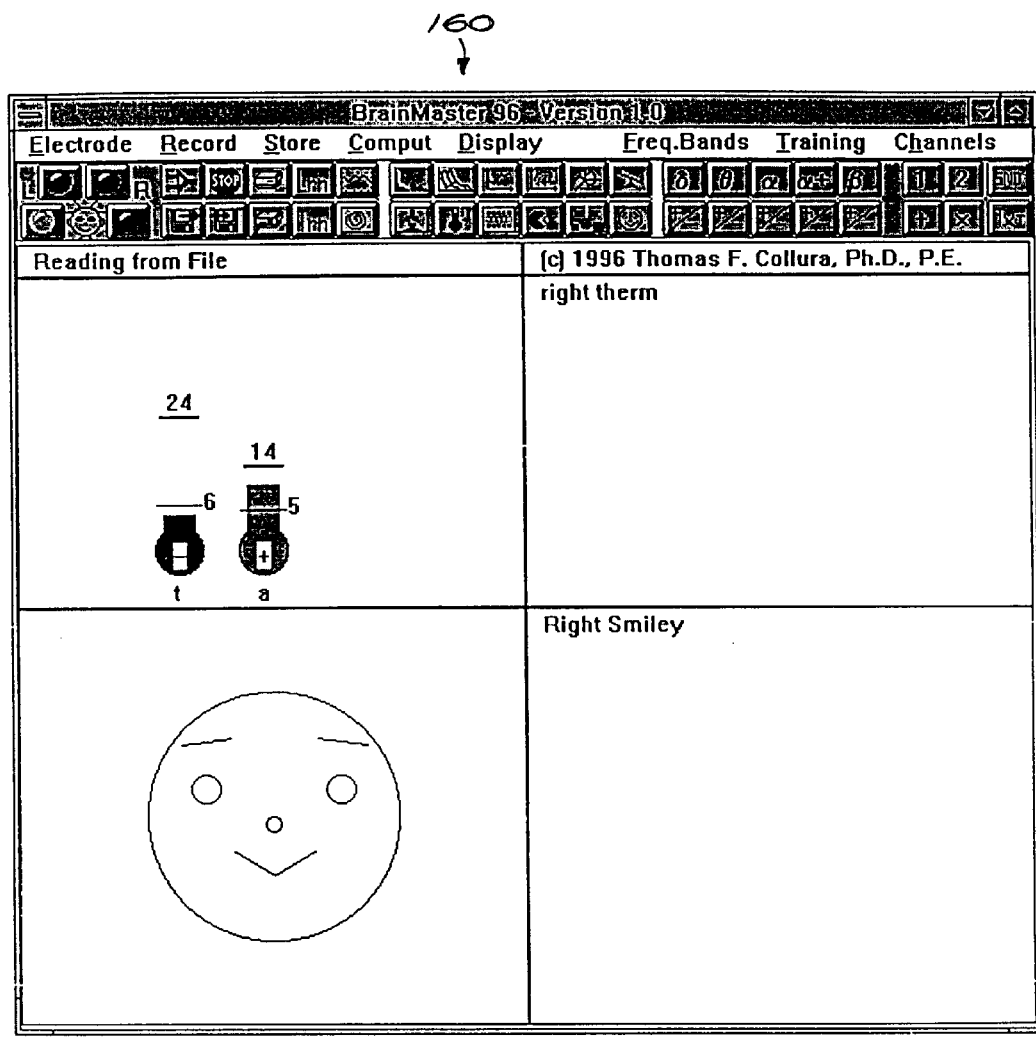
FIG. 16 is a combined screen display generated by the system of the invention.
Figure 17:
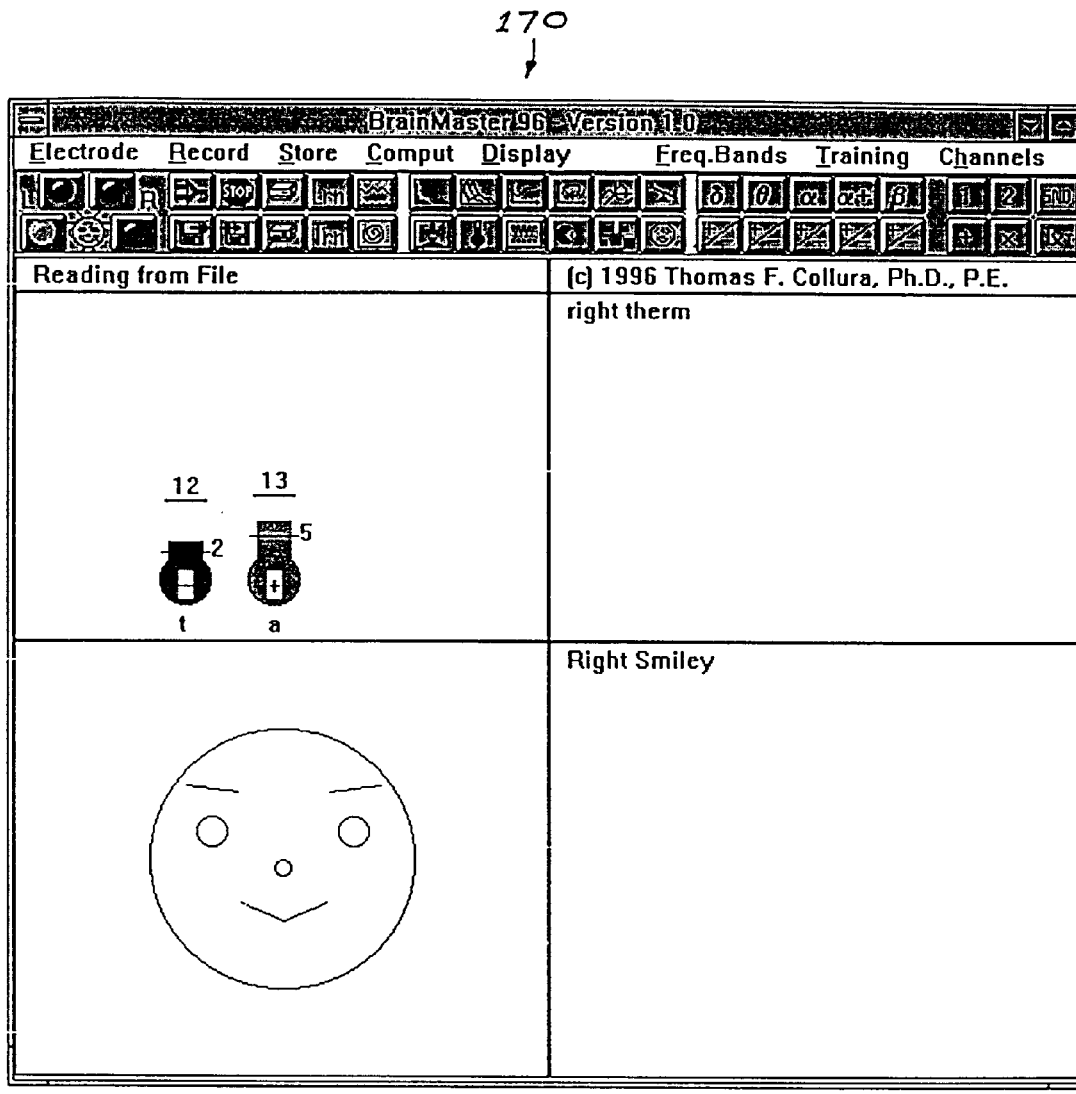
FIG. 17 is a combined screen display generated by the system of the invention.

In the display 160 of FIG. 16, the "happy" face is produced as a result of high alpha readings, and low theta readings. The mouth is smiling, and the eyebrows are lifted. Since this is what we want to see, the face is happy to see it. This image is also shown simultaneously displayed with the corresponding thermometer readings of alpha and theta. In the "mischievous" facial expression display 170 of FIG. 17 the alpha is high, but the theta is also high. As a result, the face is smiling, but the eyebrows are "scowling." The result is a mischievous look, telling the user that they still need to lower that theta! This message is emphasized by the corresponding thermometer display showing the theta column above the threshold level.

Figure 18:
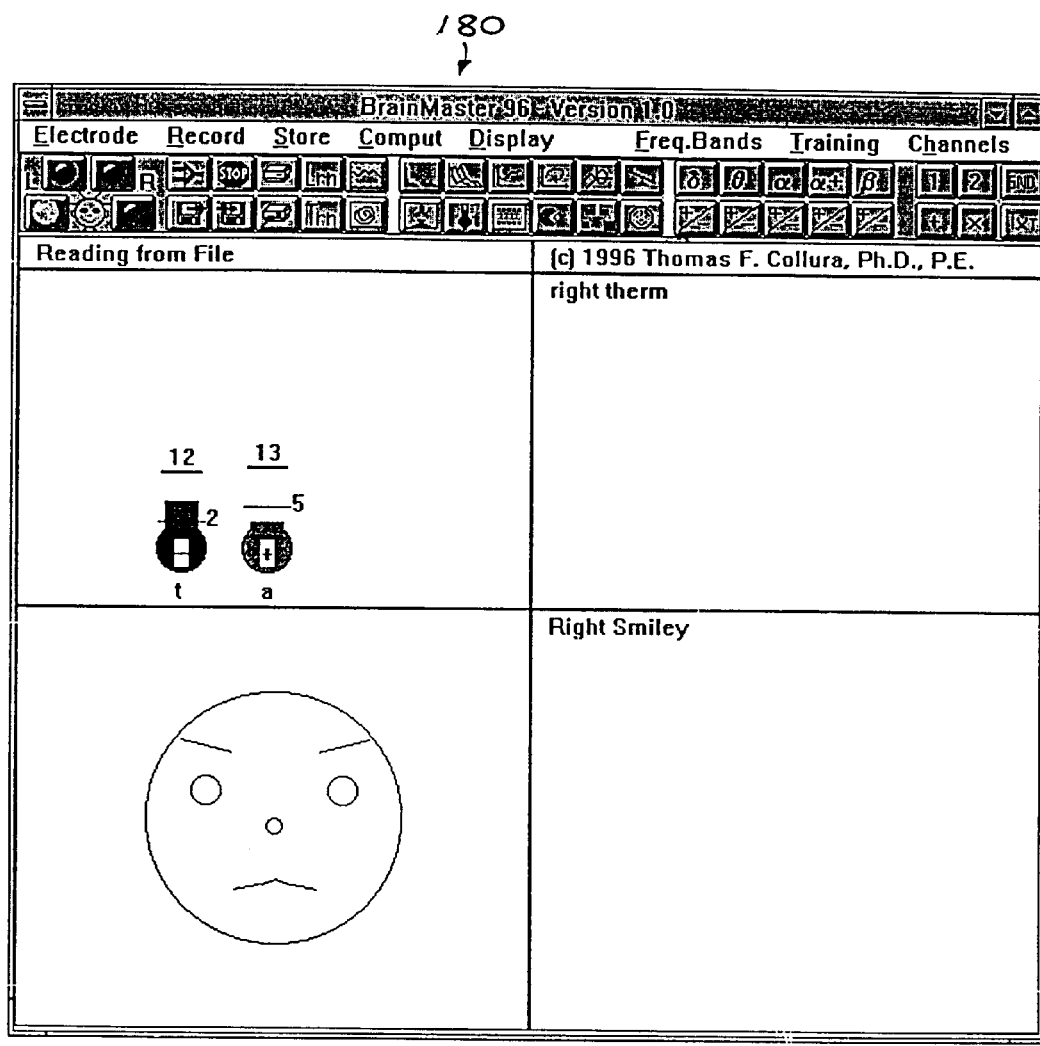
FIG. 18 is a combined screen display generated by the system of the invention.

In the "angry" facial expression display 180 of FIG. 18, the "angry" face results from low alpha, so the face is frowning. Also, the theta is high, causing the eyebrows to lower. As a result, we have a very unhappy face, telling the user that this is not at all what is desired!

As can be seen from these examples, the dynamic facial expression displays of the invention provide an extraordinary modality of biofeedback, in which the brainwave components are reflected in the apparent emotion of the visual image, providing a very direct and easy-to-comprehend display.

The facial expression display of the invention has special value, in that it has been shown that people everywhere express emotions in the same basic ways. Ekman & Friesen (1982) showed that people from different cultures interpret photographs depicting emotions in the same ways, including people as far apart as natives of New Guinea, and American college students. (Ekman P., & Friesen, W. V. (1982) Measuring facial movements with the facial action coding system. In P. Ekman (Ed.), *Emotion in the human face.* Cambridge University Press. (pp. 99, 101), and Eibl-Eibesfeldt, I. (1989) Human ethology, New York: Aldine de Gruyter. (pp. 98, 102, 116), incorporated herein by reference. Furthermore, Eibl-Eibesfeldt (1989) found that the eyebrow flash, a momentary raising of the eyebrows lasting about ⅙ second, accompanied by a smile, is universally recognized in every culture studied, including New Guinea, Samoa, Africa, Asia, South America, and Europe. This has been found to be universally recognized as a nonverbal display of happiness and surprise. This evidence has been taken to show that we come into the world genetically prepared to express and recognize emotion via facial expression. The present invention exploits this natural ability to assist in neurofeedback training by generating facial expressions which correspond and respond to detected EEG signals. By generating representations of facial expressions as displays for EEG biofeedback, the invention utilizes a basic, genetically defined communication mechanism to convey the content of the biofeedback signal.

On the tool bars of the various displays of the invention, there are provided two control buttons for each EEG component (delta, theta, alpha, alpha+, and beta) The top button has the Greek symbol for that component on it. Pressing that button will "toggle" the display and processing of that component. The corresponding "thermometer" display will appear or disappear, to indicate this.

Beneath each component button is a "+/−" button, that cycles that component through one of three states:

"ignore"=0:
display, but do not process for biofeedback
"reward"=+:
if the value exceeds threshold, send a signal.
Also, if the value is below threshold, inhibit any signal that might be sent, due to another component.
"inhibit"=−:
if the value is below threshold, send a signal.
Also, if the value is above threshold, inhibit any signal that might be send, due to another component.

The mode of each component is designated by the appearance of a "0", "+", or "−" on the corresponding thermometer bulb.

For example, to encourage high alpha, while discouraging theta, press the alpha+ button once, to change it to "+". Then, press the theta button twice, changing it to "−". A reward signal will be sent only if the alpha+ component is above threshold, and the theta component is below threshold.

If two components are assigned "+", then they must both be above threshold for a reward signal; similarly, two "−" components must both be below threshold.

The combination of "+" and "−" modes, as set up for all components is called a "paradigm."

The system of the invention has two basic operating modes for biofeedback. These are initiated by the two buttons "Lrn" and "Trn," or the "Learn" and "Train" items under the "Compute" menu heading.

"Learn" mode is as follows:

At the initiation of Learn mode, all counters, maxima, and thresholds are set to zero. The system acquires EEG, and measures the size of each component. It adjusts the maximum, and threshold, for each component, and updates these continually. No feedback is provided to the user, and no threshold crossings are counted.

At the initiation of Train mode, the maxima and thresholds are fixed. The system will provide feedback based on the paradigm set up, and will not adjust the thresholds.

The normal use is as follows:

1) Set up the desired paradigm. This can be done as the system is running in Learn mode, if desired, or before.
2) Use Learn mode to allow the BrainMaster to learn the values of your EEG components.
3) Use Train mode to allow the BrainMaster to provide you with feedback, and to count, your threshold crossings.

Although feedback is provided only when the selected paradigm is satisfied, all threshold crossings are counted with the counters. This allows the user to see the amount of each component being generated, regardless of the specific paradigm.

The system further includes a "reset" control, which is a picture of a computer with a red arrow pointing to it. This button can be used to reset the counters, and scores to zero, without changing the thresholds. The function is useful when teaching use of the feedback control screens, since it will reset the screens to zero counts, without change to the setup of any of the component controls, or their values.

Normally, when a "reward" is registered, the computer will "beep" or "ding," depending on its hardware configuration. If the "Snd" button is selected, the system will attempt to send sounds to a SoundBlaster™ (or equivalent) sound card. To use this mode, a SoundBlaster™ or functional equivalent must be installed in the computer. Preferably, the sound is a pleasant "sine" wave, with aesthetically chosen "attack" and "decay" characteristics, for a rapid, yet nondistracting, sound. The pitch of the sound is proportional to the amplitude of the component, starting at a base frequency that is different for each component. Any or all of the components can be active in this mode, allowing the user to play up to five "voices" via the EEG.

In this mode, for each component selected (visible in the "thermometer" window), a tone is generated whenever the component is above its threshold. If the threshold is kept at zero, the sound will always be heard. Thus, when training a component, the sound serves both as an audio indicator that the component is above threshold, and as an indication of the size of the component.

When processing a component for reward, but without sound, the user simply deselects "Snd" from the "thermometer" window. It will continue to be used for feedback processing, but the proportional pitch sound for that component will not be generated.

In accordance with a preferred embodiment of this aspect of the invention, the base frequencies and delta increments used for Proportional Pitch feedback are as follows:

| Component: | Base Frequency (Hz): | Delta per unit increase (Hz): |
|---|---|---|
| Delta | 100 | 5 |
| Theta | 200 | 10 |
| Alpha | 800 | 20 |
| High Alpha (SMR) | 1300 | 20 |
| Beta | 1500 | 30 |

The system of the invention also automatically maintains a file "summary" in the current directory. This file contains a textual summary of the EEG component values, their means, and standard deviations, for 2-minute intervals, or whenever the "reset" button is pressed. This file contains time-stamps with each record. In addition, when any of the number keys (1 through 9) are pressed, the file posts the exact time and date, and records the number. This allows the user to save time-markers for important events. By making a standard use of the numbered markers, up to 9 different types of events can be accurately time-logged, and the summary file compiled indefinitely.

A sample summary file as generated by the system may be as follows:

| Pass: 1: Duration: 72 seconds Tue Jun 25 23:47:28 1996 | | | | | |
|---|---|---|---|---|---|
| delta | theta | alpha | smr | beta | 40 Hz |
| min: 0 | 0 | 0 | 0 | 0 | 0 |
| max: 26 | 24 | 14 | 8 | 17 | 0 |
| mean: 14.41 | 4.92 | 7.37 | 2.89 | 6.58 | 0.00 |
| var: 14.89 | 5.91 | 8.00 | 3.24 | 7.02 | 0.00 |

| Pass: 1: Duration: 3 seconds Wed Jun 26 22:20:20 1996 | | | | | |
|---|---|---|---|---|---|
| delta | theta | alpha | smr | beta | 40 Hz |
| min: 13 | 5 | 3 | 2 | 6 | 0 |
| max: 26 | 7 | 4 | 2 | 7 | 0 |
| mean: 19.50 | 6.00 | 3.50 | 2.00 | 6.50 | 0.00 |
| var: 20.55 | 6.08 | 3.54 | 2.00 | 6.52 | 0.00 |

| Pass: 2: Duration: 4 seconds Wed Jun 26 22:20:27 1996 | | | | | |
|---|---|---|---|---|---|
| delta | theta | alpha | smr | beta | 40 Hz |
| min: 13 | 4 | 3 | 2 | 6 | 0 |
| max: 26 | 7 | 9 | 4 | 7 | 0 |
| mean: 17.33 | 5.33 | 5.33 | 2.67 | 6.67 | 0.00 |
| var: 18.38 | 5.48 | 5.94 | 2.83 | 6.68 | 0.00 |

| Pass: 3: Duration: 10 seconds Wed Jun 26 22:20:42 1996 | | | | | |
|---|---|---|---|---|---|
| delta | theta | alpha | smr | beta | 40 Hz |
| min: 13 | 3 | 2 | 1 | 6 | 0 |
| max: 26 | 9 | 9 | 7 | 9 | 0 |
| mean: 16.56 | 5.56 | 4.78 | 3.33 | 7.00 | 0.00 |
| var: 17.14 | 5.83 | 5.55 | 3.83 | 7.06 | 0.00 |

Note: 2: Wed Jun 26 22:35:25 1996
Note: 1: Wed Jun 26 22:35:28 1996

-continued

Note: 9: Wed Jun 26 22:35:32 1996

| Pass: 1: Duration: 10 seconds Wed Jun 26 22:35:35 1996 | | | | | |
|---|---|---|---|---|---|
| delta | theta | alpha | smr | beta | 40 Hz |
| min: 13 | 2 | 2 | 2 | 6 | 0 |
| max: 26 | 12 | 11 | 8 | 8 | 0 |
| mean: 15.44 | 5.44 | 6.67 | 3.89 | 6.89 | 0.00 |
| var: 15.95 | 6.06 | 7.35 | 4.31 | 6.93 | 0.00 |

The invention automatically maintains a set of "trend" files in the current directory. These are started anew, and are overwritten every time the program is started. They are named "trend0", "trend1", "trend2", and so on. They contain the amplitudes of each of the EEG components, written every second, and terminated by a <CR> <LF>. Each file contains 120 entries, and thus lasts two minutes. When a file is completed, it is finished, and the next numbered file is then created and written to. A trend file can be read at any time, even if it is the current file, since the BrainMaster program "closes" the file after each write, and "reopens" it to append data. These files are designed to be easily read and interpreted by another program, so that it can obtain up-to-date information about the EEG components being recorded.

The invention as thus described provides a novel interactive EEG biofeedback system which can be self-administered by a user to obtain direct EEG information and self-train EEG in response to the information displayed. By generating and displaying a variety of dynamic EEG signal monitoring display formats, singularly or simultaneously, the system provides a user with a selectable any single or combined EEG display paradigm, in order to achieve optimum self-training results. The novel battery-powered EEG module provides excellent mobility for connection to any suitable processor and display monitor.

A user of the system can carry out a sequence of operations suited to a specific task, including using the EEG waveform window to monitor raw EEG data, using the FFT of Mind Mirror windows to see the EEG frequency bands, using the thermometer window to monitor EEG components and set up and monitor progress of training, and using any of the other described displays to perform biofeedback procedures, and to review trends and summaries.

The system also provides certain EEG training supervisory functions so that training sessions can be self-conducted under programmed supervision, including but not limited to: (1) Instructing the user to apply electrodes and turn on the amplifier module; (2) Instructing the user to inspect and confirm the raw EEG; (3) Instructing the user to allow baseline EEG recording to proceed; (4) Instructing the user to inspect the baseline EEG frequency bands for appropriateness; (5) Entering the training mode and taking baseline component values for setting of thresholds, and (6) Instructing the user to initiate the performance of the biofeedback-related tasks. The supervisory function of the system is facilitated by internal timers in the EEG module to determine the time for each segment, and using the Report and Command display windows to provide the user with appropriate textual information. These functions may also be implemented using "spoken word" commands in the form of synthesized or stored speech, so that the biofeedback instrument can perform sufficient control and instructional activity to facilitate self-administered monitoring and biofeedback.

What is claimed is:

1. A system for self-administration of electronencephalographic (EEG) neurofeedback training through observation and control of displayed graphic images which correspond in real time to EEG signals obtained from a user of the system, the system comprising:

an EEG module having an EEG signal amplifier connected to EEG electrodes attachable to a head of a user of the system, an electrode test, auxiliary channels, an analog-to-digital converter with 8-bit digital input and output ports, rechargeable batteries and an optically isolated port for connection to a computer, the computer having an internal interrupt timer for initiating a processing cycle between the EEG module and the computer whereby acquisition and transmission of EEG data by the module is coordinated with receipt, processing and display of EEG data by the computer, and whereby coordinated processing of user feedback is enabled by transmission of user-input control information from the computer to the EEG module, system software for generating user-control functions and graphic images which correspond in real time to EEG signals received by the EEG module and processed by the computer, and a display connected to the computer for displaying graphic images generated by the system software, wherein the graphic images include a plurality of vertically oriented thermometer bars corresponding to predetermined frequency ranges of EEG signals monitored by the EEG module, and wherein the graphic images further comprise representations of facial expressions responsive to EEG signals monitored by the system the facial expressions including the facial elements of responsive representations of right and left eyebrows and lips, whereby a user connected to the EEG electrodes can receive EEG neurofeedback training by viewing the display.

2. The system of claim 1 wherein the graphic images of thermometer bars for predetermined frequency ranges of EEG signals further comprise upper and lower signal markings, the upper marking representing a maximum signal strength detected within the represented frequency range, and the lower marking representing a minimum threshold level for signal detection within the predetermined frequency range.

3. The system of claim 1 wherein the graphic images include a simultaneous display of the plurality of vertically oriented thermometer bars and at least one other form of graphic display representative of EEG signals monitored by the EEG module.

4. The system of claim 3 wherein the at least one other form of graphic display is selected from the group consisting of:

facial expression display, fast Fourier transform display, scrolling single wave form display, phase-space two-dimensional display, or compressed spectral array display, laterally opposed bifurcated display, or two-dimensional trend plot display.

5. The system of claim 4 wherein the single wave form display, laterally opposed bifurcated display, and two-dimensional trend plot display further comprise trend lines disposed about outer graphical parameters of the display to represent EEG signal trends as monitored by the EEG module.

6. The system of claim 1 wherein text is displayed on the screen, and a text marker is controlled by the software to move relative to the displayed text according to EEG signals monitored by the EEG module.

7. The system of claim 1 wherein the user-control functions include light, sound or tactile stimulators controlled by cyclic operation of command signals generated by the computer and transmitted to the EEG module.

8. The system of claim 1 wherein summary and trend information is automatically stored on a disk file and displayed to provide a user with information on time progress of EEG signals.

* * * * *